(12) United States Patent
Palushi et al.

(10) Patent No.: US 11,406,540 B2
(45) Date of Patent: Aug. 9, 2022

(54) LINKED ASSEMBLY WITH ISTHMUS ANCHOR FOR TREATING PATULOUS EUSTACHIAN TUBE

(71) Applicant: Acclarent, Inc., Irvine, CA (US)

(72) Inventors: Jetmir Palushi, Irvine, CA (US); Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 214 days.

(21) Appl. No.: 16/121,878

(22) Filed: Sep. 5, 2018

(65) Prior Publication Data

US 2020/0069472 A1  Mar. 5, 2020

(51) Int. Cl.
A61F 11/20 (2022.01)
A61L 29/16 (2006.01)
(Continued)

(52) U.S. Cl.
CPC .............. *A61F 11/202* (2022.01); *A61L 29/16* (2013.01); *A61L 31/148* (2013.01);
(Continued)

(58) Field of Classification Search
CPC ...... A61F 2210/0004; A61F 2230/0069; A61F 6/225; A61F 11/002; A61F 2002/826; A61F 2/82; A61F 2002/183; A61F 2/18; A61F 2/186; A61F 11/008; A61F 11/004; A61F 2002/821; A61F 2002/828; A61F 2002/07; A61F 2002/072; A61F 2002/075; A61F 2011/085; A61F 11/10; A61F 2/89; A61B 17/12022; A61B 17/12109; A61B 17/12036; A61B 17/12104; A61B 17/12163; A61B 17/12168; A61M 2210/0618; A61M 2210/0062; A61M 2210/0681; A61M 2210/0675; A61M 29/00; A61M 29/02
(Continued)

(56) References Cited

U.S. PATENT DOCUMENTS 4,888,017 A   12/1989   Devore et al.
5,480,433 A   1/1996   Nadol, Jr.
(Continued)

OTHER PUBLICATIONS

International Search Report and Written Opinion dated Dec. 11, 2019 for Application No. PCT/IB2019/057012, 12 pgs.

*Primary Examiner* — Kathleen S Holwerda
*Assistant Examiner* — Uyen N Vo
(74) *Attorney, Agent, or Firm* — Frost Brown Todd LLC

(57) ABSTRACT

A bio-absorbable implant is configured to bear radially outwardly against a Eustachian tube of a patient. The implant includes a proximal portion and a distal portion. The proximal portion includes an array of dilating bodies and a tether assembly. The dilating bodies are formed of a bio-absorbable material and are dimensioned to bear radially outwardly against the Eustachian tube of the patient. The tether assembly connects adjacent dilating bodies of the array of dilating bodies. The tether assembly is configured to allow restricted movement of the array of dilating bodies to thereby change the longitudinal profile of the proximal portion. The distal portion includes an anchor assembly that is configured to secure the bio-absorbable implant in the Eustachian tube of the patient.

18 Claims, 9 Drawing Sheets

(51) Int. Cl.
*A61L 31/14* (2006.01)
*A61L 27/58* (2006.01)

(52) U.S. Cl.
CPC ........... *A61F 2210/0004* (2013.01); *A61F 2230/0069* (2013.01); *A61L 27/58* (2013.01)

(58) Field of Classification Search
USPC .............. 606/109, 191, 194, 200; 623/10
See application file for complete search history.

(56) References Cited

U.S. PATENT DOCUMENTS

| | | | | |
|---|---|---|---|---|
| 5,755,781 | A * | 5/1998 | Jayaraman | A61F 2/915 623/1.16 |
| 6,251,138 | B1 | 6/2001 | Nadol, Jr. et al. | |
| 9,028,523 | B2 * | 5/2015 | Hashiba | A61B 17/3421 606/198 |
| 9,526,638 | B2 * | 12/2016 | Shalev | A61F 2/97 |
| 9,642,639 | B2 * | 5/2017 | Brady | A61B 17/22031 |
| 2002/0165601 | A1 * | 11/2002 | Clerc | A61F 2/07 623/1.13 |
| 2005/0107867 | A1 * | 5/2005 | Taheri | A61L 31/148 623/1.38 |
| 2008/0319530 | A1 * | 12/2008 | Leewood | A61F 2/07 623/1.16 |
| 2010/0076463 | A1 * | 3/2010 | Mavani | A61B 17/1219 606/151 |
| 2010/0274188 | A1 | 10/2010 | Chang et al. | |
| 2013/0006283 | A1 * | 1/2013 | Carrison | A61B 50/30 606/159 |
| 2013/0131780 | A1 * | 5/2013 | Armstrong | A61F 2/06 623/1.13 |
| 2013/0274715 | A1 | 10/2013 | Chan et al. | |
| 2015/0018934 | A1 * | 1/2015 | Pacetti | A61L 31/18 623/1.16 |
| 2015/0230915 | A1 * | 8/2015 | Farag | A61F 2/852 623/1.13 |
| 2015/0305756 | A1 * | 10/2015 | Rosenbluth | A61B 17/221 606/159 |
| 2015/0374963 | A1 | 12/2015 | Chan et al. | |
| 2017/0079761 | A1 | 3/2017 | Connors et al. | |
| 2017/0127929 | A1 | 5/2017 | Schutt et al. | |

* cited by examiner

LINKED ASSEMBLY WITH ISTHMUS ANCHOR FOR TREATING PATULOUS EUSTACHIAN TUBE

BACKGROUND

Referring to FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. A narrowed region known as the isthmus (29) of the ET (26) provides a transition between the remainder of the ET (26) and the middle ear (14). The isthmus (29) is the narrowest part of the ET (26) at the junction of the bony and cartilaginous parts of the ET (26) (i.e., where the bony canal meets the cartilaginous tube). The isthmus (29) thus has a reduced inner diameter compared to the remaining portion of the ET (26) that extends between the isthmus (29) and the pharyngeal ostium (28); and provides a density that is substantially greater than the density of the tissue of the remaining portion of the ET (26) that extends between the isthmus (29) and the pharyngeal ostium (28).

The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This may occur frequently in children in connection with an upper respiratory infection and account for hearing impairment associated with this condition.

When the ET (26) is blocked, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Finally, the fluid can become infected, which can lead to pain, illness, and temporary hearing loss. If the inner ear (16) is affected, the patient may feel a spinning or turning sensation (vertigo).

Methods for treating the middle ear (14) and restriction or blockage of the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pub. No. 2015/0374963, entitled "Vent Cap for a Eustachian Tube Dilation System," published Dec. 31, 2015, issued as U.S. Pat. No. 10,350,396 on Jul. 16, 2019, the disclosure of which is incorporated by reference herein.

In some cases, rather than being restricted or blocked, the ET (26) may fail to close properly, or such that the ET (26) takes an inordinately prolonged amount of time to close after being opened, such that the ET (26) substantially remains in a patulous state. This may adversely affect the patient by causing variations in the upper airway pressure around the ET (26) and the middle ear (14). In some patients, a patulous ET (26) may create a feeling of dry sinus, an increased breathing rate with physical activity, higher than usual perceived volumes of sound, and/or other undesirable consequences. It may therefore be desirable to provide a form of treatment for a patulous ET (26). It may further be desirable for such a treatment to still provide some degree of ventilation and drainage for the ET (26), without completely closing the ET (26).

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
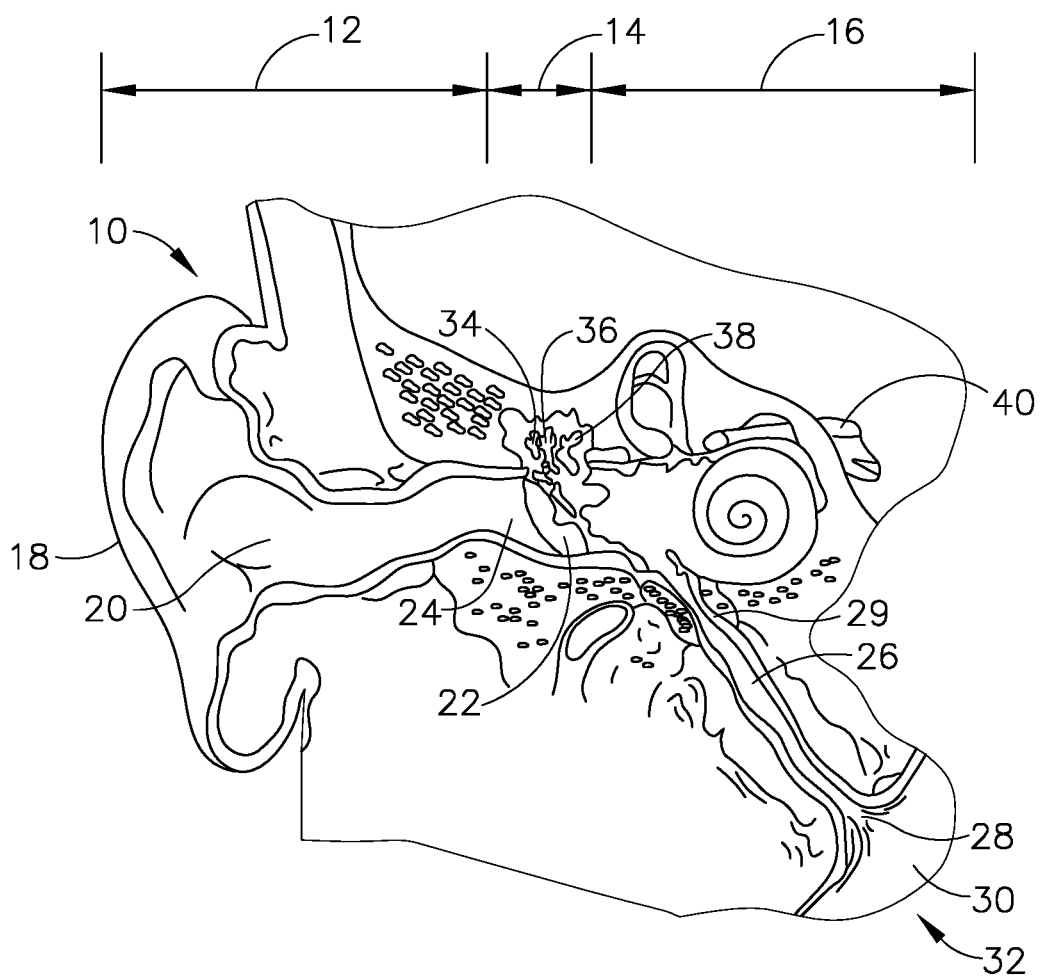
FIG. 1 depicts a cross-sectional view of a human ear showing the inner, middle and outer ear portions and the Eustachian tube connecting the middle ear with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Method of Treating the Eustachian Tube

As noted above, some patients may have an ET (26) that remains patulous for a prolonged period, which may be undesirable for various reasons. In some instances, if a patulous ET (26) is maintained in a radially outwardly stressed state (as comparted to ET (26) in the patulous state) for a prolonged period of time (e.g. nine to twelve months), the prolonged stress may trigger a process were cells within ET (26) regenerate such that ET (26) transitions from the undesirable patulous state toward a more desirable, normal functioning state. For instance, imposing a radially outward stress on the ET (26) may generate scar tissue in the ET (26). It may therefore be desirable to insert an implant or other device into a patulous ET (26) of a patient, where the inserted implant or other device is capable of bearing radially outwardly against the sidewall of a patulous ET (26) for a prolonged period of time.

When an implant or other device is inserted and/or located within a patulous ET (26) of the patient for a prolonged period of time, the implant may cause discomfort or pain for a multitude of reasons, such as due to the rigidity of the implant along a longitudinal profile. Therefore, it may also be desirable to have an implant or other device that is sufficiently laterally flexible to conform to the anatomy shape of a patulous ET (26), or various other anatomical passageway, after or during deployment. Further, it may be desirable to have an implant or other device that is made of bio-absorbable materials configured to bio-absorb after a desired prolonged period of time, such that there is no need for removal of the implant or other device after deployment.

The following description provides various examples of devices that may be deployed within the ET (26) to bear outwardly against the inner diameter of the ET (26) for a prolonged period of time. Other suitable ways in which the below-described devices may be used will be apparent to those of ordinary skill in the art in view of the teachings herein.

Figure 2:
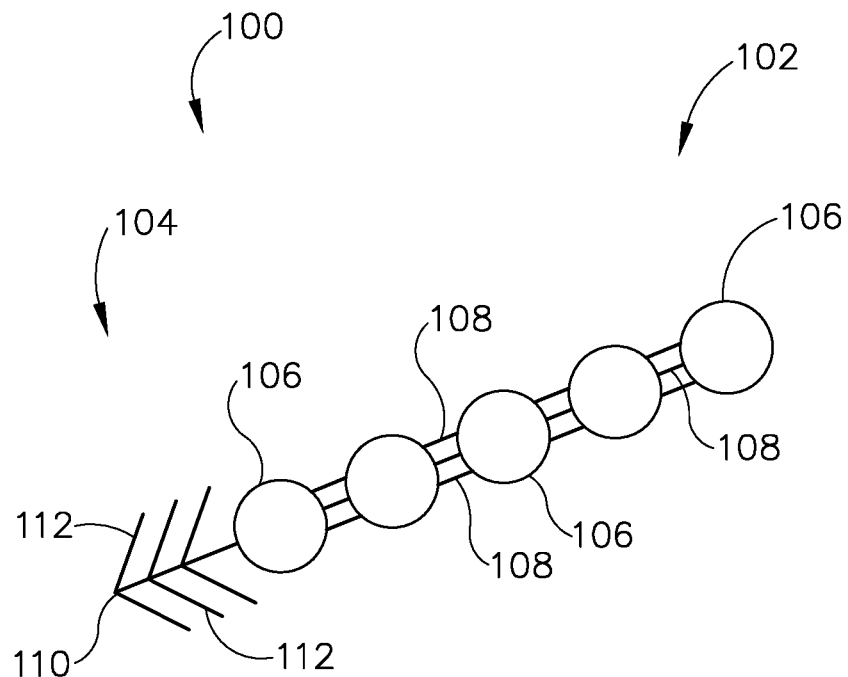
FIG. 2 depicts a side elevational view of an exemplary implant.

FIG. 2 shows an exemplary implant (100) that may be deployed within ET (26). Implant (100) extends along a longitudinal dimension from a proximal portion (102) to a distal portion (104). As will be described in greater detail below, proximal portion (102) is dimensioned to bear against ET (26) of the patient, and in some cases slightly expand or stretch ET (26) of the patient, when suitably deployed. As will also be described in greater detail below, distal portion (104) is dimensioned to be inserted within isthmus (29) and is configured to attach to isthmus (29) of the patient to help promote stability of a deployed implant (100) within ET (26).

Proximal portion (102) includes an array of bio-absorbable spheres (106) connected to each other in a linear array via connecting suture (108). While spheres (106) are used in the present example, spheres (106) may be replaced with structures having any other suitable shape(s). Bio-absorbable spheres (106) are dimensioned to abut against an interior wall (27) of ET (26) when implant (100) is suitably deployed such that spheres (106) bear radially outwardly against ET (26). Bio-absorbable spheres (106) may have any suitable dimension as would be apparent to one having ordinary skill in the art in view of the teachings herein. For instance, bio-absorbable spheres (106) may have a diameter ranging from approximately 1 millimeters and approximately 5 millimeters. Additionally, one bio-absorbable sphere (106) may have different dimensions compared to other bio-absorbable spheres (106) of the same implant (100). For instance, bio-absorbable spheres (106) may have outer diameters that progressively reduce or increase along the length of implant (100), thereby providing implant (100) with a generally tapered longitudinal profile. Bio-absorbable spheres (106) may be resiliently flexible such that spheres (106) may transition between a naturally expanded state (as shown in FIGS. 2 and 4C) and a compressed state (as shown in FIG. 4B). Bio-absorbable spheres (106) may be radially compressed and axially lengthened when in the compressed state as compared to the naturally expanded state.

In the present example, bio-absorbable spheres (106) may be in the compressed state while contained within a sheath (50) during deployment of implant (100). Spheres (106) may then naturally return to the expanded state when no longer contained within sheath (50). As will be described in greater detail below, containing bio-absorbable spheres (106) within sheath (50) during deployment of implant (100) may allow bio-absorbable spheres (106) to be initially inserted within the desired location of ET (26) without causing unnecessary discomfort for the patient. While bio-absorbable spheres (106) are sufficiently resilient to transition between the naturally expanded state and the compressed state, bio-absorbable spheres (106) may also be sufficiently resilient such that when deployed within ET (26), spheres (106) maintain sufficient contact with interior wall (27) to suitably bear radially outwardly against ET (26). In other words, bio-absorbable spheres (106) are sufficiently flexible to transition into the compressed state within the confines of sheath (50), but also sufficiently resilient to bear radially outwardly against interior wall (27) of ET (26) while in the expanded state.

Bio-absorbable spheres (106) may be made from a bio-absorbable material configured to completely absorb after deployment of implant (100) after any suitable period of time that would be apparent to one having ordinary skill in the art in view of the teachings herein. As one example, bio-absorbable spheres (106) may be formed from a material configured to completely absorb after about nine to twelve months. Bio-absorbable spheres (106) may have any suitable geometric configuration as would be apparent to one having ordinary skill in the art in view of the teachings herein. For example, bio-absorbable spheres (106) may have a solid sphere-like shape, a hollow spherical shell shape, a cylindrical shape, an ellipsoidal shape, etc. In the current example, proximal portion (102) has five bio-absorbable spheres (106). However, any suitable number of bio-absorbable spheres (106) may be used as would be apparent to one having ordinary skill in the art in view of the teachings herein. In some variations, spheres (106) may include ventilation passageways that enable fluid communication between pharyngeal ostium (28) and isthmus (29), thereby providing a ventilation pathway between the middle ear (14) and the nasopharynx (30) while implant (100) is installed in the ET (26).

Connecting suture (108) extends between bio-absorbable spheres (106) such that bio-absorbable spheres (106) are tethered to adjacent spheres (106). Additionally, connecting sutures (108) are suitably laterally bendable and or flexible to allow bio-absorbable spheres (106) to easily move relative to each other, thereby changing the longitudinal profile of proximal portion (102) of implant (100). Connecting sutures (108) are also short enough such that the distance between adjacent spheres (106) is suitable for spheres (106) to provide the needed expansion of ET (26) when implant is suitably deployed. Connecting sutures (108) may also be made of any suitable bio-absorbable material as would be apparent to one having ordinary skill in the art in view of the teachings herein. In the present example, connecting sutures (108) are non-extensible.

In some versions, connecting sutures (108) are separate, discrete pieces extending between adjacent pairs of spheres (106), such that each suture (108) terminates in the adjacent spheres (106). In addition, or in the alternative, one, more than one, or all sutures (108) may extend along the full length of proximal portion (102), such that one, more than one, or all sutures (108) span through all spheres (106). In some such versions, spheres (106) may slide longitudinally along the one or more sutures (108) extending through spheres (106). Other suitable relationships between spheres (106) and sutures (108) will be apparent to those of ordinary skill in the art in view of the teachings herein.

While the longitudinal profile of proximal portion (102) is shown with bio-absorbable spheres (106) in a linear arrangement, bio-absorbable spheres (106) may move relative to each other to form other suitable longitudinal profiles, such as an S-shaped arrangement. Therefore, when implant (100) is suitably deployed with ET (26), bio-absorbable spheres (106) may contact interior wall (27) of ET (26) in such a manner that spheres (106) conform to the longitudinal profile of ET (26). The flexible longitudinal profile may help reduce pain and or discomfort experienced by the patient during or after implant (100) has been deployed within ET (26). In the current example, three connecting sutures (108) extend between each pair of adjacent bio-absorbable spheres (106). However, any other suitable number of connecting sutures (108) may be used as would be apparent to one having ordinary skill in the art in view of the teachings herein. Additionally, different connecting sutures (108) may have different levels of flexibility as would be apparent to one having ordinary skill in the art in view of the teachings herein.

Distal portion (104) includes a distal barbed suture (110) and a plurality of barbs (112), which may both be formed of any suitable bio-absorbable material as would be apparent to one having ordinary skill in the art in view of the teachings herein. Distal barbed suture (110) extends from the most distal bio-absorbable sphere (106). Barbed suture (110) is dimensioned for insertion within isthmus (29) of patient when implant (100) is deployed. Barbs (112) are connected to and extend away from distal barbed suture (110). In the present example, barbs (112) extend outwardly and proximally along respective axes that are oblique to the central longitudinal axis of implant (100). Barbs (112) are configured to anchor to isthmus (29) when deployed such that implant (100) is secured within ET (26).

Barbs (112) are resiliently flexible to transition between a natural expanded state (as shown in FIGS. 2 and 4C) and a compressed state (as shown in FIG. 4B). Barbs (112) may be contained within a sheath (50) in the compressed state during deployment of implant (100), and then naturally return to the expanded state when barbs (112) are no longer contained within sheath (50). In some other variations, barbs (112) are not compressed within sheath (50); and are merely contained within sheath (50) until deployment. Barbs (112) may be configured to anchor to isthmus (29) by penetrating portions of isthmus (29). Alternatively, barbs (112) may be configured anchor to isthmus (29) via any other suitably means as would be apparent to one having ordinary skill in the art in view of the teachings herein. For instance, barbs (112) may be configured to abut against interior wall of isthmus (29) with sufficient frictional forces to anchor implant (100).

While in the current example, barbs (112) extend away from barbed suture (110) in a linear fashion, barbs (112) and suture (110) may have any geometrical arrangement as would be apparent to one having ordinary skill in the art in view of the teachings herein. As one example, suture (110) and barbs (112) may be replaced with a helical coil with spikes disposed about coil such that coil abuts against isthmus (29) while spikes penetrate isthmus (29).

The entirety of implant (100) or selected portions of implant (100) may be coated or otherwise implemented with any suitable drug or therapeutic agent as would be apparent to one having ordinary skill in the art in view of the teachings herein. For example, bio-absorbable spheres (106) may be coated with a therapeutic agent. As another mere example, barbs (112) may be coated with a therapeutic agent.

Figure 4A:
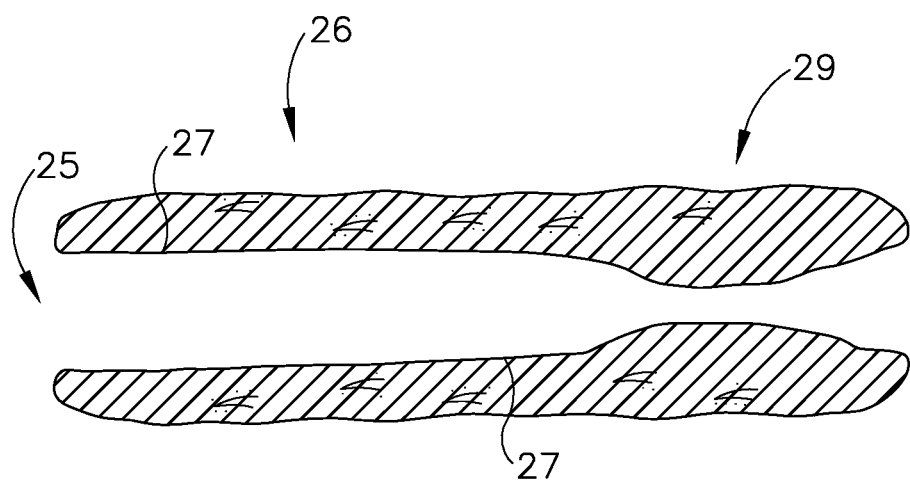
FIG. 4A depicts a cross-sectional view of a patulous Eustachian tube of the patient.
Figure 4B:
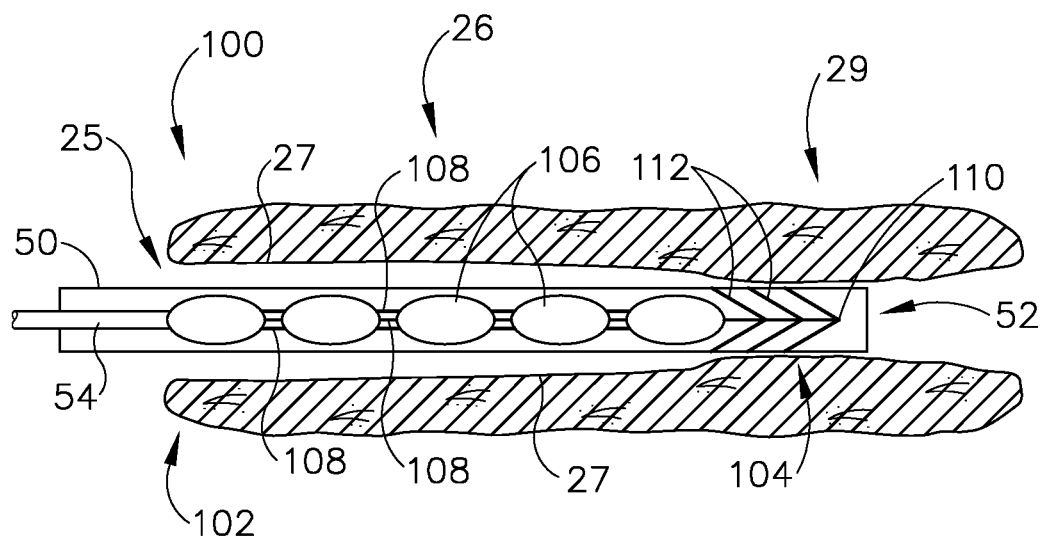
FIG. 4B depicts a cross-sectional view of the Eustachian tube of FIG. 4A, with a sheath slidably advanced therein, the sheath containing the implant of FIG. 2 therein, with the Eustachian tube implant restricted to the compressed state by the sheath.
Figure 4C:
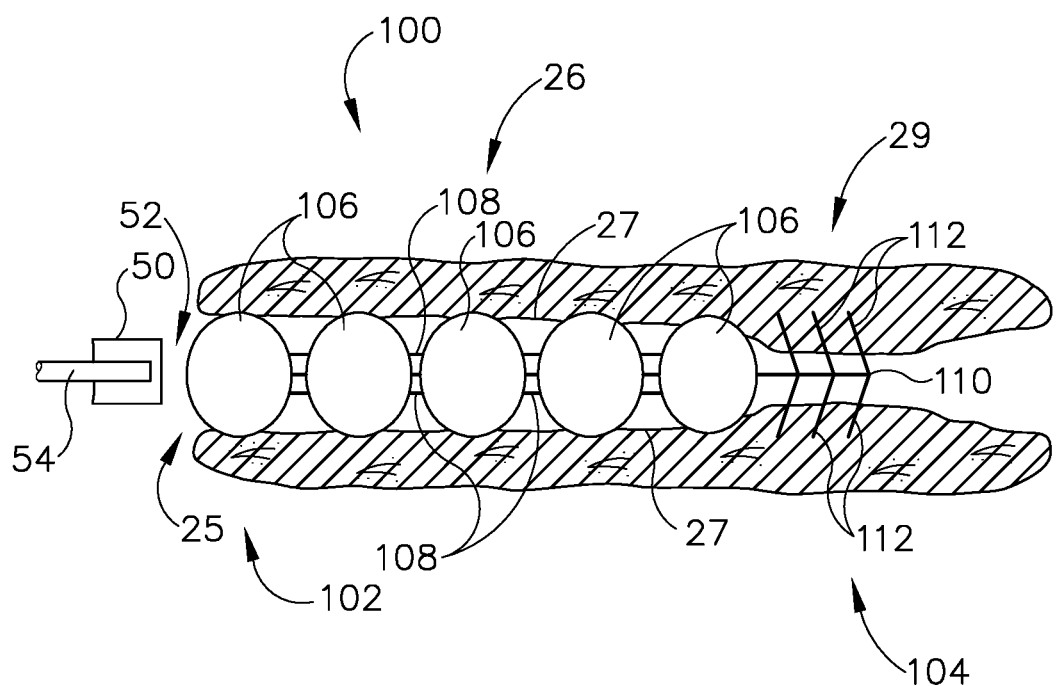
FIG. 4C depicts a cross-sectional view of the Eustachian tube of FIG. 4A, where the sheath of FIG. 4B is slidably removed, and with the implant of FIG. 2 inserted within the Eustachian tube thereby bearing against the sidewall of the Eustachian tube.

FIGS. 4A-4D show an exemplary deployment and use of implant (100) with a patulous ET (26). FIG. 4A shows ET (26) in a patulous state. First, as shown in FIG. 4B, an operator may advance a deployment mechanism containing implant (100) transnasally or transorally into ET (26) via the pharyngeal ostium (28). In the present example, deployment mechanism includes a sliding sheath (50) comprising an open distal end (52), and a push rod (54) located within the confines of sliding sheath (50). Sliding sheath (50) is advanced within channel (25) of ET (26) until distal barbed suture (110) is located directly adjacent to isthmus (29) as shown in FIG. 4B. Any suitable deployment mechanism may be used as would be apparent to one having ordinary skill in the art in view of the teachings herein.

Implant (100) is located within sliding sheath (50) such that distal barbed suture (110) is located proximal to open distal end (52) of sliding sheath (50) such that barbs (112) are in the compressed state (or are otherwise contained) within sliding sheath (50). Similarly, bio-absorbable spheres (106) are confined in the compressed state within sliding sheath (50). A distal end of push rod (54) may be adjacent to the most proximal bio-absorbable sphere (106) when sliding sheath (50) is advanced into ET (26). When implant (100) is positioned within ET (26) at the desired location, the operator may utilize a deployment mechanism to suitably deploy implant (100) within ET (26). In the current example, the operator may slide sheath (50) proximally while push rod (54) remains stationary in contact with the proximal most bio-absorbable sphere (106). Push rod (54) therefore keeps implant (100) longitudinally stationary within ET (26) while sheath (50) is retracted proximally relative to ET (26). Alternatively, the operator may actuate push rod (54) distally while keeping sheath (50) stationary, thereby distally advancing implant (100) out of open distal end (52) of sheath (50).

Figure 4D:
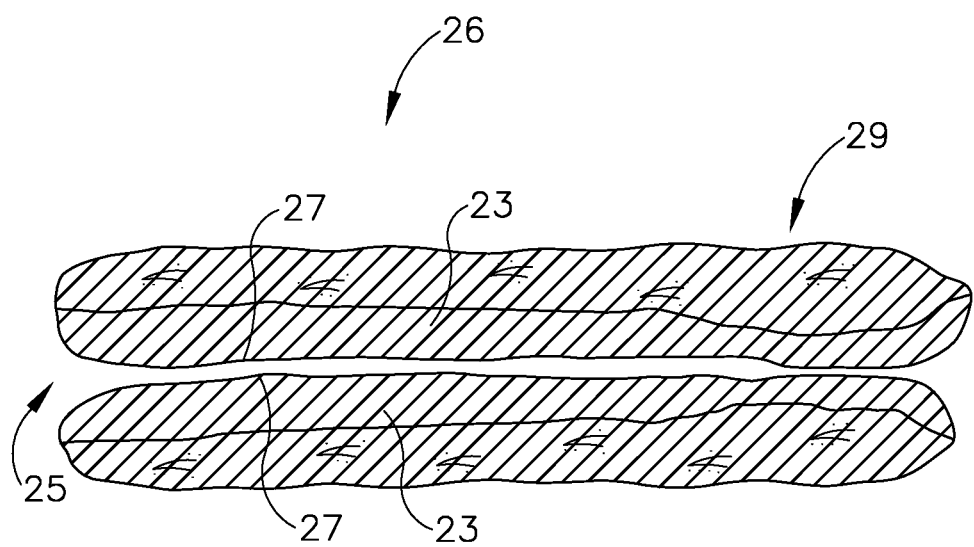
FIG. 4D depicts a cross-sectional view of the Eustachian tube of FIG. 4A in a normally functioning state after the implant of FIG. 2 has been bio-absorbed, where the Eustachian tube has regenerated cell growth.

Either way, when implant (100) is deployed, as shown in FIG. 4C, distal barbs (112) and bio-absorbable spheres (106) are no longer constrained in the compressed position such that barbs (112) and spheres (106) resiliently return toward the natural expanded position. In the current example, with barbs (112) in the natural expanded position, barbs (112) penetrate isthmus (29) to help initially anchor implant (100) within ET (26). As mentioned above, spheres (106) bear radially outwardly against interior wall (27) of ET (26) in the natural expanded position, while connecting sutures (108) allow sphere (106) to move relative to each other such that spheres (106) conform to a longitudinal profile similar to that of ET (26). The radial stress imposed by spheres (106) on interior wall (27) causes the generation of additional tissue (23) in the ET (26). After a suitable period of time, as shown in FIG. 4D, implant (100) is bio-absorbed into adjacent anatomy. The additional tissue (23) remains in the ET (26), thereby providing ET (26) in a non-patulous state. In other words, the additional tissue (23) generated in response to stress imposed by spheres (106) results in ET (26) in a normal functioning state.

Figure 5A:
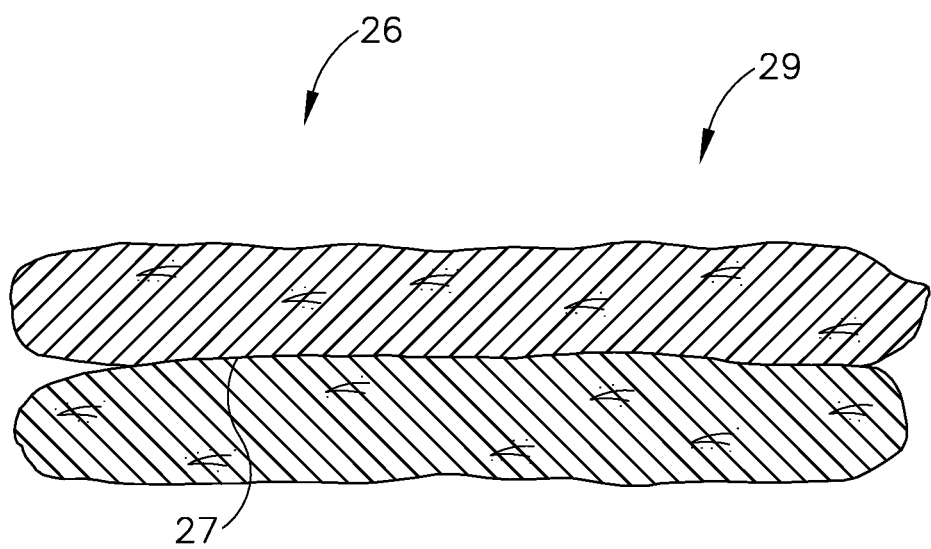
FIG. 5A depicts a cross-sectional view of a closed Eustachian tube of the patient.
Figure 5B:
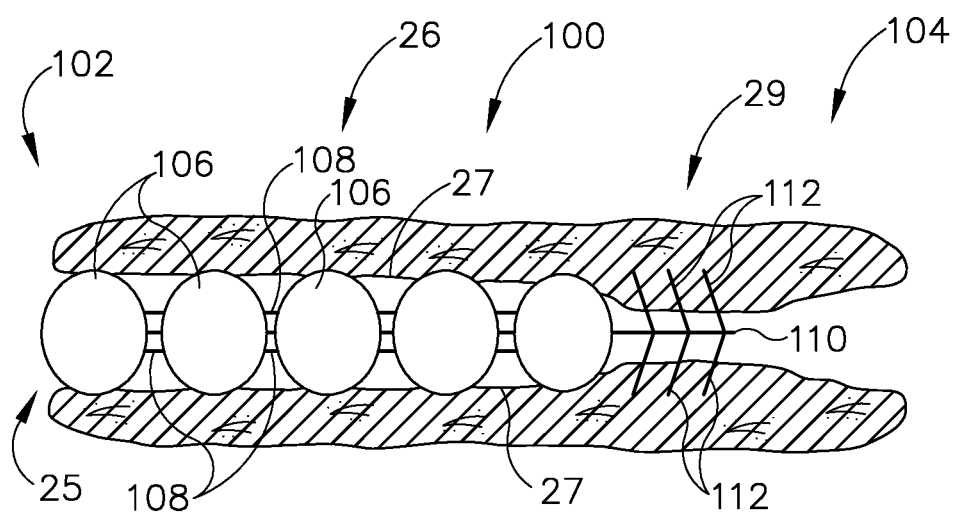
FIG. 5B depicts a cross-sectional view of the Eustachian tube of FIG. 5A, where the implant of FIG. 2 is inserted within the Eustachian tube thereby dilating the side walls of the Eustachian tube.
Figure 5C:
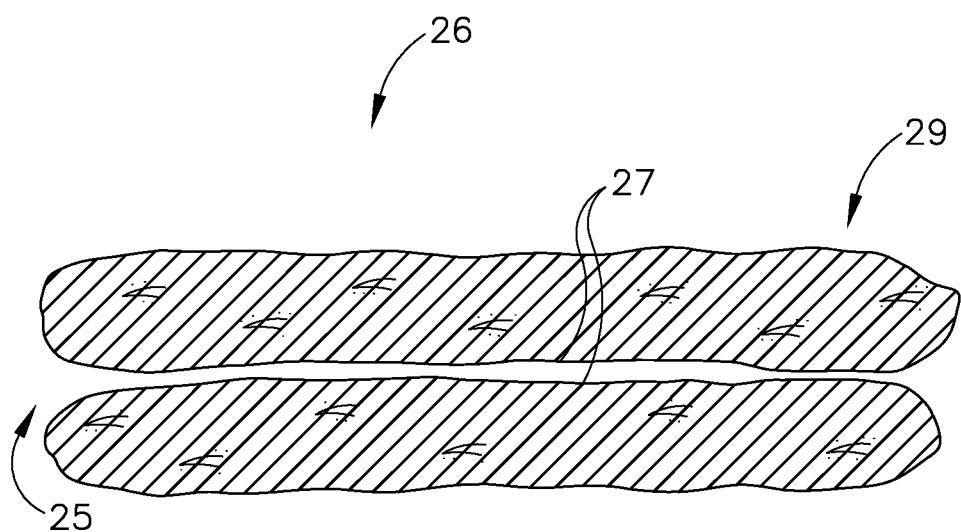
FIG. 5C depicts a cross-sectional view of the Eustachian tube of FIG. 5A in a normally functioning state after the implant of FIG. 2 has been bio-absorbed.

FIGS. 5A-5C shows an exemplary use of implant (100) to help treat a ET (26) that is persistently closed. FIG. 5A shows ET (26) that is persistently closed such that interior wall (27) acts as its own obstruction. As shown in FIG. 5B, the operator may deploy implant (100) within ET (29) such that distal barbed suture (110) is located directly adjacent to isthmus (29) and spheres (106) are within ET (26), expanding interior wall (27). Connecting sutures (108) may allow spheres (106) to move relative each other in order to conform to the longitudinal profile of ET (29). Spheres (106) may bear against interior wall (27) in a manner sufficient to effectively dilate the ET (26). After a suitable period of time, implant (100) may bio-absorb into the anatomy of the patient, with ET (26) being sufficiently dilated to thereby operate in a normal functioning state.

Figure 3:
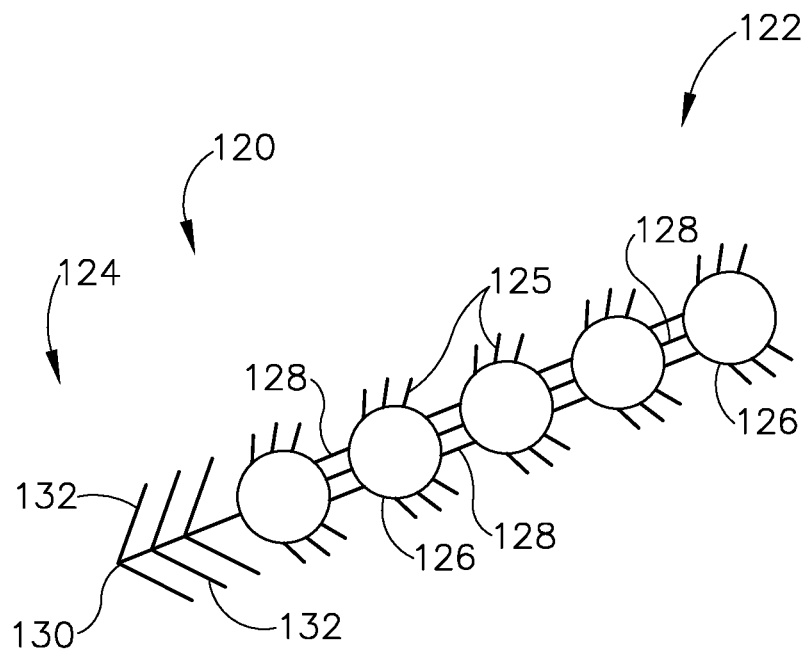
FIG. 3 depicts a side elevational view of another exemplary implant.

FIG. 3 shows an exemplary alternative implant (120) that may used in place of implant (100) described above. Implant (120) is substantially similar to implant (100) described above, with differences elaborated below. Implant (120) extends from a proximal portion (122) to a distal portion (124). Distal portion (124) is substantially similar to distal portion described above. Therefore, distal portion (124) includes a barbed suture (130) with a plurality of barbs (132) that are substantially similar to barbed suture (110) and barbs (112) described above. Proximal portion (122) includes a plurality of bio-absorbable spheres (126) connected to adjacent spheres (126) via connecting suture (128). Spheres (126) and connected suture (128) are substantially similar to spheres (106) and connecting suture (108) described above, with differences elaborated below. In particular, a plurality of barbs (125) extends from an exterior surface of spheres (126). Barbs (125) are configured to anchor to corresponding sections of ET (26) when deployed such that implant (120) is further secured within ET (26). Barbs (125) are resiliently flexible to transition between a natural expanded state and a compressed state. In particular, barbs (125) may be contained within a sheath (50) in the compressed state during deployment of implant (120), and then naturally return to the expanded state when barbs (125) are no longer contained within sheath (50). Barbs (125) may be configured to assist distal barbed suture (130) in anchoring implant (120) to ET (26) by penetrating portions of ET (26).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A bio-absorbable implant configured to bear radially outwardly against a Eustachian tube of a patient, the bio-absorbable implant comprising: (a) a proximal portion defining a longitudinal profile, the proximal portion comprising: (i) an array of dilating bodies formed of a bio-absorbable material, wherein the array of dilating bodies are dimensioned to bear radially outwardly against the Eustachian tube of the patient, and (ii) a tether assembly connecting adjacent dilating bodies of the array of dilating bodies, wherein the tether assembly is configured to allow restricted movement of the array of dilating bodies to thereby change the longitudinal profile of the proximal portion; and (b) a distal portion comprising an anchoring assembly, wherein the anchoring assembly is configured to secure the bio-absorbable implant in the Eustachian tube of the patient.

Example 2

The bio-absorbable implant of Example 1, wherein the array of dilating bodies are configured to transition between an expanded state and a compressed state.

Example 3

The bio-absorbable implant of Example 2, wherein the array of dilating bodies are resiliently biased toward the expanded state.

Example 4

The bio-absorbable implant of any one or more of Examples 1 through 3, wherein the array of dilating bodies comprises a plurality of spheres.

Example 5

The bio-absorbable implant of Example 4, wherein each of the spheres has an outer diameter dimensioned at or between approximately 1 millimeters and approximately 5 millimeters.

Example 6

The bio-absorbable implant of any one or more of Examples 1 through 5, wherein the tether assembly comprises a plurality of bio-absorbable suture elements.

Example 7

The bio-absorbable implant of Example 6, wherein the at least one bio-absorbable suture element in the plurality of bio-absorbable suture elements extends between adjacent dilating bodies.

Example 8

The bio-absorbable implant of any one or more of Examples 1 through 7, wherein the array of dilating bodies are coated with a therapeutic agent.

Example 9

The bio-absorbable implant of any one or more of Examples 1 through 8, wherein the array of dilating bodies further comprises a therapeutic agent embedded into the bio-absorbable material.

Example 10

The bio-absorbable implant of any one or more of Examples 1 through 9, wherein the distal portion further comprises a distally extending suture member.

Example 11

The bio-absorbable implant of Example 10, wherein the anchoring member further comprises a plurality of barbs connected to the distally extending suture member.

Example 12

The bio-absorbable implant of Example 11, wherein the plurality of barbs are resilient.

Example 13

The bio-absorbable implant of any one or more of Examples 1 through 12, wherein the array of dilating bodies further comprises a plurality of barbs.

Example 14

The bio-absorbable implant of any one or more of Examples 1 through 13, wherein the array of dilating bodies comprises at least five dilating bodies.

Example 15

The bio-absorbable implant of any one or more of Examples 1 through 14, further comprising a sheath configured to maintain the dilating bodies in a radially compressed state.

Example 16

A bio-absorbable implant configured bear radially outwardly against a Eustachian tube of a patient, the bio-absorbable implant comprising: (a) a proximal portion defining a flexible longitudinal profile, the proximal portion comprising: (i) an array of bio-absorbable dilating bodies, wherein the array of bio-absorbable dilating bodies are dimensioned to bear radially outwardly against the Eustachian tube of the patient, and (ii) a connecting assembly connecting adjacent bioabsorbable dilating bodies of the array of bio-absorbable dilating bodies, wherein the connecting assembly is configured to allow restricted movement of the array of bio-absorbable dilating bodies relative to other dilating bodies in the of dilating bodies; and (b) a distal portion comprising an anchoring assembly, wherein the anchoring assembly is configured to engage the Eustachian tube of the patient.

Example 17

The bio-absorbable implant of Example 16, wherein the connecting assembly is coated in a therapeutic agent.

Example 18

The bio-absorbable implant of any one or more of Examples 16 through 17, wherein the array of bio-absorbable dilating bodies are resiliently flexible.

Example 19

The bio-absorbable implant of any one or more of Examples 16 through 18, wherein the distal portion further comprise a distally extending suture.

Example 20

A bio-absorbable implant configured to bear radially outwardly against a Eustachian tube of a patient, the bio-absorbable implant comprising: (a) a proximal portion defining a longitudinal profile, the proximal portion comprising an array of dilating bodies comprising a bio-absorbable material, wherein the array of dilating bodies are dimensioned to bear radially outwardly against the Eustachian tube of the patient, wherein the array of dilating bodies are attached to adjacent dilating bodies such that each dilating body in the array of dilating bodies may move relative to each other to change the longitudinal profile of the proximal portion; and (b) a distal portion comprising an anchoring assembly, wherein the anchoring assembly is configured to secure the bio-absorbable implant in the Eustachian tube of the patient.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A bio-absorbable implant configured to bear radially outwardly against a Eustachian tube of a patient, the bio-absorbable implant comprising:
   (a) a proximal portion defining a longitudinal profile, the proximal portion comprising:
      (i) an array of dilating bodies formed of a bio-absorbable material, wherein the array of dilating bodies are dimensioned to bear radially outwardly against the Eustachian tube of the patient, wherein the array of dilating bodies comprises a plurality of spheres, wherein each of the spheres has an outer diameter dimensioned at or between approximately 1 millimeter and approximately 5 millimeters, and
      (ii) a tether assembly connecting adjacent dilating bodies of the array of dilating bodies, wherein the tether assembly is configured to allow restricted movement of the array of dilating bodies to thereby change the longitudinal profile of the proximal portion; and
   (b) a distal portion comprising an anchoring assembly, wherein the anchoring assembly comprises a plurality of barbs configured to penetrate an isthmus of the Eustachian tube of the patient to thereby secure the bio-absorbable implant in the Eustachian tube of the patient,
   wherein the proximal portion and the distal portion are configured to define a ventilation pathway between a middle ear and a nasopharynx of the patient while bearing radially outwardly against the Eustachian tube.

2. The bio-absorbable implant of claim 1, wherein the array of dilating bodies are configured to transition between an expanded state and a compressed state.

3. The bio-absorbable implant of claim 2, wherein the array of dilating bodies are resiliently biased toward the expanded state.

4. The bio-absorbable implant of claim 1, wherein the tether assembly comprises a plurality of bio-absorbable suture elements.

5. The bio-absorbable implant of claim 4, wherein at least one bio-absorbable suture element in the plurality of bio-absorbable suture elements extends between adjacent dilating bodies.

6. The bio-absorbable implant of claim 1, wherein the array of dilating bodies is coated with a therapeutic agent.

7. The bio-absorbable implant of claim 1, wherein the array of dilating bodies further comprises a therapeutic agent embedded into the bio-absorbable material.

8. The bio-absorbable implant of claim 1, wherein the distal portion further comprises a distally extending suture member.

9. The bio-absorbable implant of claim 8, wherein the plurality of barbs are connected to the distally extending suture member.

10. The bio-absorbable implant of claim 9, wherein the plurality of barbs are resilient.

11. The bio-absorbable implant of claim 1, wherein the array of dilating bodies further comprises a plurality of barbs.

12. The bio-absorbable implant of claim 1, wherein the array of dilating bodies comprises at least five dilating bodies.

13. The bio-absorbable implant of claim 1, further comprising a sheath configured to maintain the dilating bodies in a radially compressed state.

14. A bio-absorbable implant configured bear radially outwardly against a Eustachian tube of a patient, the bio-absorbable implant comprising:
  (a) a proximal portion defining a flexible longitudinal profile, the proximal portion comprising:
    (i) an array of bio-absorbable dilating bodies, wherein the array of bio-absorbable dilating bodies are dimensioned to bear radially outwardly against the Eustachian tube of the patient, wherein the array of dilating bodies comprises a plurality of spheres, wherein each of the spheres has an outer diameter dimensioned at or between approximately 1 millimeter and approximately 5 millimeters and
    (ii) a connecting assembly connecting adjacent bioabsorbable dilating bodies of the array of bio-absorbable dilating bodies, wherein the connecting assembly is configured to allow restricted movement of the array of bio-absorbable dilating bodies relative to other dilating bodies in the of dilating bodies; and
  (b) a distal portion comprising an anchoring assembly, wherein the anchoring assembly comprises a barb configured to engage and penetrate the Eustachian tube of the patient to thereby secure the bio-absorbable implant to the Eustachian tube,
  wherein the proximal portion and the distal portion are configured to define a ventilation pathway along the entire length of the Eustachian tube of the patient while initially implanted.

15. The bio-absorbable implant of claim 14, wherein the connecting assembly is coated in a therapeutic agent.

16. The bio-absorbable implant of claim 14, wherein the array of bio-absorbable dilating bodies is resilient flexible.

17. The bio-absorbable implant of claim 14, wherein the distal portion further comprises a distally extending suture.

18. A bio-absorbable implant configured to bear radially outwardly against a Eustachian tube of a patient, the bio-absorbable implant comprising:
  (a) a proximal portion defining a longitudinal profile, the proximal portion comprising an array of dilating bodies comprising a bio-absorbable material, wherein the array of dilating bodies are dimensioned to bear radially outwardly against the Eustachian tube of the patient, wherein the array of dilating bodies are attached to adjacent dilating bodies such that each dilating body in the array of dilating bodies may move relative to each other to change the longitudinal profile of the proximal portion, wherein the array of dilating bodies comprises a plurality of spheres, wherein each of the spheres has an outer diameter dimensioned at or between approximately 1 millimeter and approximately 5 millimeters; and
  (b) a distal portion comprising an anchoring assembly, wherein the anchoring assembly comprises a plurality of resilient barbs configured to penetrate an isthmus of the Eustachian tube of the patient to secure the bio-absorbable implant in the Eustachian tube of the patient, wherein the proximal portion and the distal portion are configured to define a ventilation pathway between a first end and a second end of the Eustachian tube while the bio-absorbable implant is secured to the Eustachian tube.

\* \* \* \* \*